US012642591B2

(12) United States Patent
Leist

(10) Patent No.: US 12,642,591 B2
(45) **Date of Patent: \*Jun. 2, 2026**

(54) ANATOMICAL STRUCTURE VISUALIZATION SYSTEMS AND METHODS

(71) Applicant: Intuitive Surgical Operations, Inc., Sunnyvale, CA (US)

(72) Inventor: Liron Leist, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/901,429

(22) Filed: Sep. 30, 2024

(65) Prior Publication Data

US 2025/0090231 A1    Mar. 20, 2025

Related U.S. Application Data

(63) Continuation of application No. 17/290,173, filed as application No. PCT/US2019/058387 on Oct. 28, 2019, now Pat. No. 12,127,792.

(Continued)

(51) Int. Cl.
*A61B 34/10* (2016.01)
*A61B 34/00* (2016.01)
(Continued)

(52) U.S. Cl.
CPC .............. *A61B 34/10* (2016.02); *A61B 34/25* (2016.02); *A61B 34/30* (2016.02); *A61B 34/70* (2016.02);
(Continued)

(58) Field of Classification Search
CPC ......... A61B 34/10; A61B 34/25; A61B 34/30; A61B 34/70; A61B 90/37;
(Continued)

(56) References Cited

U.S. PATENT DOCUMENTS 9,220,468 B2   12/2015  Kitamura et al.
9,585,569 B2   3/2017   Itai
(Continued)

OTHER PUBLICATIONS

International Preliminary Report on Patentability for Application No. PCT/US2019/058387, mailed on May 14, 2021, 10 pages.
(Continued)

*Primary Examiner* — John R Schnurr

(57) ABSTRACT

In certain examples, an anatomical structure visualization system determines a distance between a point on an anatomical surface visible to an endoscope and a point on an embedded anatomical object that is visually occluded from the viewpoint of the endoscope by the anatomical surface. The anatomical structure visualization system may determine, based on the determined distance, a display parameter for a pixel of an image representative of a view of the anatomical surface from the viewpoint of the endoscope and assign the determined display parameter to the pixel of the image. The anatomical structure visualization system may similarly determine and assign display parameters to other pixels of the image and provide the image for display. The displayed image may provide a visualization of an anatomical structure at a surgical area, including a visualization of how deep the embedded anatomical object is positioned from the anatomical surface.

20 Claims, 8 Drawing Sheets

Related U.S. Application Data

(60) Provisional application No. 62/752,457, filed on Oct. 30, 2018.

(51) Int. Cl.
*A61B 34/30* (2016.01)
*A61B 90/00* (2016.01)

(52) U.S. Cl.
CPC ........ *A61B 90/37* (2016.02); *A61B 2034/102* (2016.02); *A61B 2034/107* (2016.02); *A61B 2034/301* (2016.02)

(58) Field of Classification Search
CPC ........ A61B 2034/102; A61B 2034/107; A61B 2034/301; G06T 2210/41; G06T 15/503
See application file for complete search history.

(56) References Cited

U.S. PATENT DOCUMENTS

| | | | |
|---|---|---|---|
| 9,808,145 B2 | 11/2017 | Sakuragi | |
| 9,830,737 B2 | 11/2017 | Sakuragi | |
| 12,127,792 B2 * | 10/2024 | Leist | A61B 34/30 |
| 2011/0082667 A1 | 4/2011 | Ibarz et al. | |
| 2015/0269741 A1 | 9/2015 | Moriya | |
| 2017/0007350 A1 | 1/2017 | Popovic et al. | |
| 2017/0237958 A1 | 8/2017 | Themelis | |
| 2019/0082942 A1 | 3/2019 | Kutsuma | |
| 2020/0015906 A1 | 1/2020 | Scheib et al. | |
| 2021/0378748 A1 | 12/2021 | Leist | |
| 2023/0065264 A1 | 3/2023 | Popovic et al. | |
| 2023/0218356 A1 | 7/2023 | Azizian et al. | |

OTHER PUBLICATIONS

International Search Report and Written Opinion for Application No. PCT/US2019/058387, mailed on Jan. 21, 2020, 13 pages.

Marques B., et al., "Improving Depth Perception during Surgical Augmented Reality," SIGGRAPH, Aug. 2015, pp. Article No. 24, XP055656229, 2 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

Wang R., et al., "Visualization Techniques for Augmented Reality in Endoscopic Surgery," Medical Imaging and Augmented Reality (MIAR2016), XP047357185, Aug. 14, 2016, pp. 129-138.

Winnie C., et al., "Overlay Visualization in Endoscopic ENT Surgery," International Journal of Computer Assisted Radiology and Surgery, Jun. 2010, vol. 6 (3), pp. 401-406.

* cited by examiner

500

502

Display
Parameter

Distance

600

602

Display
Parameter

Distance

ANATOMICAL STRUCTURE VISUALIZATION SYSTEMS AND METHODS

RELATED APPLICATIONS

The present application is a continuation of U.S. patent application Ser. No. 17/290,173, filed Apr. 29, 2021, which is a U.S. National Stage Application under 35 U.S.C. § 371 of International Application No. PCT/US2019/058387, filed Oct. 28, 2019, which claims priority to U.S. Provisional Patent Application No. 62/752,457, filed Oct. 30, 2018, each of which is hereby incorporated by reference in its entirety.

BACKGROUND INFORMATION

During a computer-assisted surgical procedure, such as a minimally invasive surgical procedure that uses a computer-assisted surgical system, an endoscope may be used to capture endoscopic imagery of a surgical area. The computer-assisted surgical system may display the captured endoscopic imagery to medical personnel (e.g., to a surgeon and/or other members of a surgical team) to provide a visualization of the surgical area. The visualized surgical area assists the medical personnel in performing the surgical procedure. However, there remains room to improve visualizations of surgical areas and technologies used to provide visualizations of surgical areas during a surgical procedure.

SUMMARY

An exemplary system includes a processor and a memory communicatively coupled to the processor and storing instructions executable by the processor to determine a distance, along a line extending from a viewpoint of an endoscope in a three-dimensional space, between a point on an anatomical surface visible to the endoscope and a point on an embedded anatomical object visually occluded from the viewpoint of the endoscope by the anatomical surface, determine, based on the determined distance, a display parameter for a pixel of an image representative of a view of the anatomical surface from the viewpoint of the endoscope, the pixel corresponding to the point on the anatomical surface, and assign the determined display parameter to the pixel of the image.

An exemplary computer-assisted surgical system includes at least one physical computing device communicatively coupled to a stereoscopic endoscope and a display device, the at least one physical computing device configured to determine a distance between a point on an anatomical surface visible to the endoscope and a point on an embedded anatomical object visually occluded from the viewpoint of the endoscope by the anatomical surface, determine, based on the determined distance, a display parameter for a pixel of an image representative of a view of the anatomical surface from the viewpoint of the endoscope, the pixel corresponding to the point on the anatomical surface, and provide the image for display by the display device, the image including the pixel displayed in accordance with the display parameter.

An exemplary method includes determining, by an anatomical structure visualization system, a distance, along a line extending from a viewpoint of an endoscope in a three-dimensional space, between a point on an anatomical surface visible to the endoscope and a point on a modeled anatomical object visually occluded from the viewpoint of the endoscope by the anatomical surface, determining, by the anatomical structure visualization system and based on the determined distance, a display parameter for a pixel of an image representative of a view of the anatomical surface from the viewpoint of the endoscope, the pixel corresponding to the point on the anatomical surface, and assigning, by the anatomical structure visualization system, the determined display parameter to the pixel of the image.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
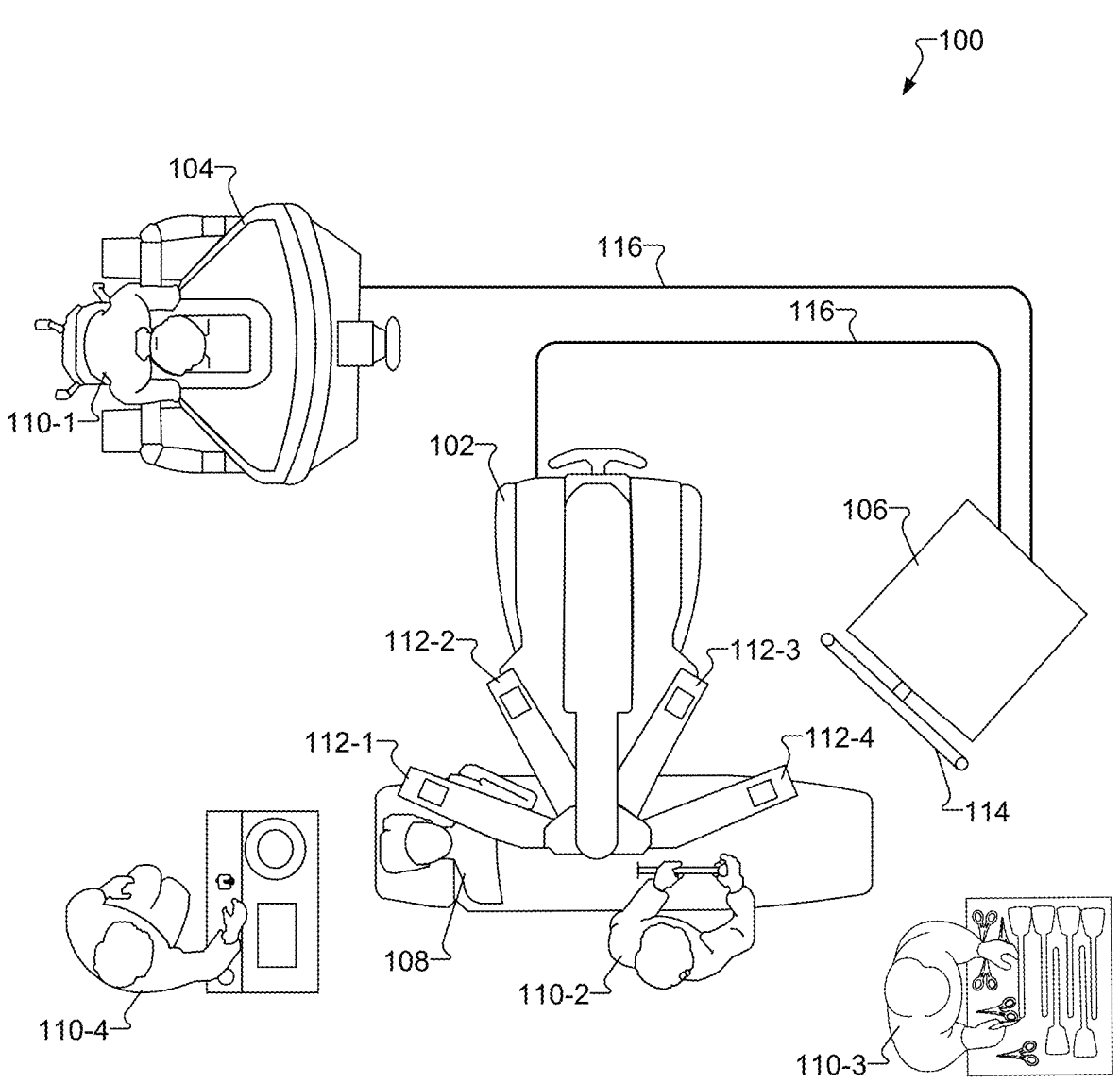
FIG. 1 illustrates an exemplary computer-assisted surgical system according to principles described herein.

Anatomical structure visualization systems and methods are described herein. Exemplary anatomical structure visualization systems and methods described herein may be implemented by a computer-assisted surgical system and may provide a visualization of an anatomical structure at a surgical area during a surgical procedure. As described herein, the visualization may represent and visually indicate depth of the anatomical structure, such as the depth of an embedded anatomical object from an anatomical surface of the anatomical structure, in a manner that is intuitive and helpful to a surgical team member such as a surgeon.

In certain examples, an anatomical structure visualization system may determine a distance between a point on an anatomical surface visible to an endoscope and a point on an embedded anatomical object that is visually occluded from the viewpoint of the endoscope by the anatomical surface. The anatomical structure visualization system may determine, based on the determined distance, a display parameter for a pixel of an image representative of a view of the anatomical surface from the viewpoint of the endoscope and assign the determined display parameter to the pixel of the image. The anatomical structure visualization system may similarly determine and assign display parameters to other pixels of the image and provide the image for display. The displayed image may provide a visualization of an anatomical structure at a surgical area, including a visualization of how deep the embedded anatomical object is positioned from the anatomical surface.

To this end, in certain examples, the display parameters of the pixels of the image may be determined in a manner that increases, within an image, visual emphasis of an embedded anatomical object that is relatively more proximate to the anatomical surface and decreases, within an image, visual emphasis of an embedded anatomical object that is relatively less proximate to the anatomical surface. Thus, a degree of visual emphasis of the embedded anatomical object in the image may visually represent depth of the embedded anatomical object from the anatomical surface of the anatomical structure. Examples of the anatomical structure visualization system determining display parameters of pixels of an image are described herein.

In certain examples, the anatomical structure visualization system provides user controls for use by a surgical team member to adjust settings of the anatomical structure visualization system. As an example, user controls may facilitate adjustment of settings that modify how depth of an embedded anatomical object is visually indicated in an image. For example, user controls may be used by a surgical team member to adjust the display parameters of an image and/or how the display parameters are determined by the anatomical structure visualization system. In certain examples, for instance, user controls may allow a surgical team member to adjust a maximum depth within which an embedded anatomical object is visually represented in an image and beyond which an embedded anatomical object is not visually represented in an image, a minimum value of a display parameter (e.g., a minimum visibility) that sets a minimum visual emphasis that is to be displayed for an embedded anatomical object represented in an image, and/or a prominence multiplier that adjusts a degree of visual emphasis that is used to visually represent an embedded anatomical object in an image. In certain examples, one or more of the user controls described herein may facilitate real-time adjustment of settings to allow settings to be adjusted by a surgical team member on-the-fly during a surgical procedure.

In certain examples, the anatomical structure visualization system provides user controls for use by a surgical team member to toggle between display modes provided by the anatomical structure visualization system. As an example, user controls may facilitate toggling between a plurality of display modes, which may include a mode for visualization of only surface anatomy visible to an endoscope, a mode for concurrent visualization of surface anatomy visible to the endoscope and embedded anatomy that may be hidden from the view of the endoscope, and a mode for visualization of only embedded anatomy. In certain examples, one or more of the user controls described herein may facilitate real-time toggling of display modes to allow display modes to be toggled by a surgical team member on-the-fly during a surgical procedure.

Anatomical structure visualization systems and methods described herein may operate as part of or in conjunction with a computer-assisted surgical system. As such, in order to promote an understanding of anatomical structure visualization systems and methods described herein, an exemplary computer-assisted surgical system will now be described. The described exemplary computer-assisted surgical system is illustrative and not limiting. Anatomical structure visualization systems and methods described herein may operate as part of or in conjunction with the computer-assisted surgical system described herein and/or with other suitable computer-assisted surgical systems.

FIG. 1 illustrates an exemplary computer-assisted surgical system 100 ("surgical system 100"). As shown, surgical system 100 may include a manipulating system 102, a user control system 104, and an auxiliary system 106 communicatively coupled one to another. Surgical system 100 may be utilized by a surgical team to perform a computer-assisted surgical procedure on a patient 108. As shown, the surgical team may include a surgeon 110-1, an assistant 110-2, a nurse 110-3, and an anesthesiologist 110-4, all of whom may be collectively referred to as "surgical team members 110." Additional or alternative surgical team members may be present during a surgical session as may serve a particular implementation.

While FIG. 1 illustrates an ongoing minimally invasive surgical procedure, it will be understood that surgical system 100 may similarly be used to perform open surgical procedures or other types of surgical procedures that may similarly benefit from the accuracy and convenience of surgical system 100. Additionally, it will be understood that the surgical session throughout which surgical system 100 may be employed may not only include an operative phase of a surgical procedure, as is illustrated in FIG. 1, but may also include preoperative, postoperative, and/or other suitable phases of the surgical procedure. A surgical procedure may include any procedure in which manual and/or instrumental techniques are used on a patient to investigate or treat a physical condition of the patient.

As shown in FIG. 1, manipulating system 102 may include a plurality of manipulator arms 112 (e.g., manipulator arms 112-1 through 112-4) to which a plurality of surgical instruments may be coupled. Each surgical instrument may be implemented by any suitable surgical tool (e.g., a tool having tissue-interaction functions), medical tool, monitoring instrument (e.g., an endoscope), sensing instrument (e.g., a force-sensing surgical instrument), diagnostic instrument, or the like that may be used for a computer-assisted surgical procedure on patient 108 (e.g., by being at least partially inserted into patient 108 and manipulated to perform a computer-assisted surgical procedure on patient 108). While manipulating system 102 is depicted and described herein as including four manipulator arms 112, it will be recognized that manipulating system 102 may include only a single manipulator arm 112 or any other number of manipulator arms as may serve a particular implementation.

Manipulator arms 112 and/or surgical instruments attached to manipulator arms 112 may include one or more displacement transducers, orientational sensors, and/or positional sensors used to generate raw (i.e., uncorrected) kinematics information. One or more components of surgical system 100 may be configured to use the kinematics information to track (e.g., determine positions of) and/or control the surgical instruments.

Surgical instruments attached to manipulator arms 112 may each be positioned at a surgical area associated with a patient. As used herein, a "surgical area" associated with a patient may, in certain examples, be entirely disposed within the patient and may include an area within the patient near where a surgical procedure is planned to be performed, is being performed, or has been performed. For example, for a minimally invasive surgical procedure being performed on tissue internal to a patient, the surgical area may include the tissue, anatomy underlying the tissue, as well as space around the tissue where, for example, surgical instruments being used to perform the surgical procedure are located. In other examples, a surgical area may be at least partially disposed external to the patient. For instance, surgical system 100 may be used to perform an open surgical procedure such that part of the surgical area (e.g., tissue being operated on) is internal to the patient while another part of the surgical area (e.g., a space around the tissue where one or more surgical instruments may be disposed) is external to the patient. A surgical instrument may be referred to as being located at or within a surgical area when at least a portion of the surgical instrument (e.g., a distal end of the surgical instrument) is located within the surgical area.

User control system 104 may be configured to facilitate control by surgeon 110-1 of manipulator arms 112 and surgical instruments attached to manipulator arms 112. For example, surgeon 110-1 may interact with user control system 104 to remotely move or manipulate manipulator arms 112 and the surgical instruments. To this end, user control system 104 may provide surgeon 110-1 with imagery (e.g., high-definition 3D imagery) of a surgical area associated with patient 108 as captured by an endoscope. In certain examples, user control system 104 may include a stereo viewer having two displays where stereoscopic images of a surgical area associated with patient 108 and generated by a stereoscopic endoscope may be viewed by surgeon 110-1. Surgeon 110-1 may utilize the imagery to perform one or more procedures with one or more surgical instruments attached to manipulator arms 112.

To facilitate control of surgical instruments, user control system 104 may include a set of master controls. These master controls may be manipulated by surgeon 110-1 to control movement of surgical instruments (e.g., by utilizing robotic and/or teleoperation technology). The master controls may be configured to detect a wide variety of hand, wrist, and finger movements by surgeon 110-1. In this manner, surgeon 110-1 may intuitively perform a procedure using one or more surgical instruments.

Auxiliary system 106 may include one or more computing devices configured to perform primary processing operations of surgical system 100. In such configurations, the one or more computing devices included in auxiliary system 106 may control and/or coordinate operations performed by various other components (e.g., manipulating system 102 and user control system 104) of surgical system 100. For example, a computing device included in user control system 104 may transmit instructions to manipulating system 102 by way of the one or more computing devices included in auxiliary system 106. As another example, auxiliary system 106 may receive, from manipulating system 102, and process image data representative of imagery captured by an endoscope attached to one of manipulator arms 112.

In some examples, auxiliary system 106 may be configured to present visual content to surgical team members 110 who may not have access to the images provided to surgeon 110-1 at user control system 104. To this end, auxiliary system 106 may include a display monitor 114 configured to display one or more user interfaces, such as images (e.g., 2D images) of the surgical area, information associated with patient 108 and/or the surgical procedure, and/or any other visual content as may serve a particular implementation. For example, display monitor 114 may display images of the surgical area together with additional content (e.g., graphical content, contextual information, etc.) concurrently displayed with the images. In some embodiments, display monitor 114 is implemented by a touchscreen display with which surgical team members 110 may interact (e.g., by way of touch gestures) to provide user input to surgical system 100.

Manipulating system 102, user control system 104, and auxiliary system 106 may be communicatively coupled one to another in any suitable manner. For example, as shown in FIG. 1, manipulating system 102, user control system 104, and auxiliary system 106 may be communicatively coupled by way of control lines 116, which may represent any wired or wireless communication link as may serve a particular implementation. To this end, manipulating system 102, user control system 104, and auxiliary system 106 may each include one or more wired or wireless communication interfaces, such as one or more local area network interfaces, Wi-Fi network interfaces, cellular interfaces, etc.

Figure 2:
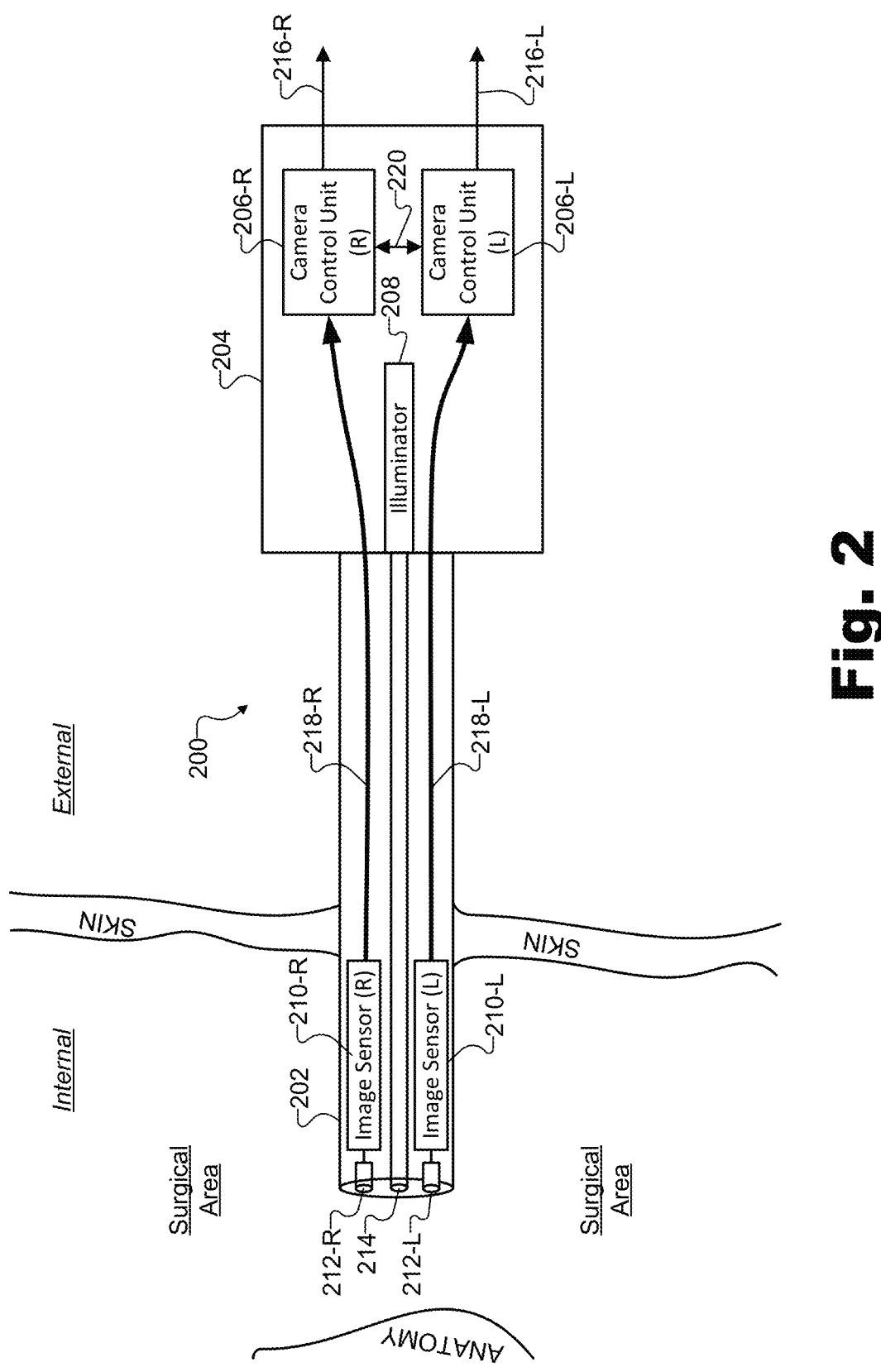
FIG. 2 illustrates an exemplary stereoscopic endoscope located at a surgical area associated with a patient according to principles described herein.

FIG. 2 illustrates an exemplary stereoscopic endoscope 200. Endoscope 200 may be manually controlled (e.g., by a surgeon performing a surgical procedure on a patient). Alternatively, endoscope 200 may be coupled to a manipulator arm (e.g., one of manipulator arms 112) of a computer-assisted surgical system (e.g., surgical system 100), and controlled using robotic and/or teleoperation technology. Endoscope 200 is representative of many different types and/or implementations of endoscopes that may be used with systems and methods described herein.

As shown, endoscope 200 includes a shaft 202 and a camera head 204 coupled to a proximal end of shaft 202. Camera head 204 is configured to be located external to the patient. Shaft 202 has a distal end that is configured to be positioned at (e.g., inserted into) a surgical area of a patient. In various implementations, shaft 202 is rigid (as shown in FIG. 2). Alternatively, shaft 202 may be jointed and/or flexible.

As shown, camera head 204 houses a right-side camera control unit 206-R, a left-side camera control unit 206-L, and an illuminator 208. In some alternative examples, camera control units 206 and illuminator 208 are not included in camera head 204 and are instead located in an endoscope controller communicatively coupled to endoscope 200. The endoscope controller may be implemented by auxiliary system 106, for example.

Shaft 202 houses a right-side image sensor 210-R optically coupled to a right-side optic 212-R, a left-side image sensor 210-L optically coupled to a left-side optic 212-L, and an illumination channel 214. The right-side components (i.e., camera control unit 206-R, image sensor 210-R, and optic 212-R) implement a camera that captures images 216-R of the surgical area from a right-side perspective. Likewise, the left-side components (i.e., camera control unit 206-L, image sensor 210-L, and optic 212-L) implement a camera that captures images 216-L of the surgical area from a left-side perspective.

To capture images 216, illuminator 208 generates light, which is carried by one or more optical fibers in illumination channel 214 and output into the surgical area at a distal end of shaft 202. Optics 212, which may each be implemented by a lens or other suitable component, capture the light after the light reflects from patient anatomy and/or other objects within the surgical area.

The light captured by optics 212 is sensed by image sensors 210. Image sensors 210 may be implemented as any suitable image sensors such as charge coupled device ("CCD") image sensors, complementary metal-oxide semi-conductor ("CMOS") image sensors, or the like. Image sensors 210-R and 210-L convert the sensed light into signals (e.g., video data) representative of images, and transmit the signals to camera control units 206 by way of conduits 218-R and 218-L, respectively. Conduits 218 may be any suitable communication link configured to handle high-speed transmission of data.

Camera control units 206 process the signals received from image sensors 210 and generate, based on the signals, data representative of images 216. Camera control units 206 then transmit the data to an external device (e.g., a computing device that processes the images and/or displays the images and/or video formed by the images on a display screen). As shown, camera control units 206 are synchronously coupled to one another by way of a communicative link 220 so that images 216 are synchronized.

Additional or alternative components may be included in endoscope 200. For example, one or more other optics not explicitly shown in FIG. 2 may be included in shaft 202 for focusing, diffusing, or otherwise treating light generated and/or sensed by endoscope 200. In some alternative examples, image sensors 210 can be positioned closer to the proximal end of shaft 202 or inside camera head 204, a configuration commonly referred to as a rod lens endoscope.

Endoscope 200 may provide data representing visible light data of a surgical area. For example, endoscope 200 may capture visible light images of the surgical area that represent visible light sensed by endoscope 200. Visible light images may include images that use any suitable color and/or grayscale palette to represent a visible light based view of the surgical area.

Endoscope 200 may also provide data representing depth data of a surgical area or data that may be processed to derive depth data of the surgical area. For example, endoscope 200 may capture images of the surgical area that represent depth sensed by endoscope 200. Alternatively, endoscope 200 may capture images of the surgical area that may be processed to derive depth data of the surgical area. For example, images 216-R and 216-L may be stereoscopic images of the surgical area, which images may be processed to determine depth information for the surgical area. The depth information may be represented as depth images (e.g., depth map images obtained using a Z-buffer that indicates distance from endoscope 200 to each pixel point on an image of a surgical area), which may be configured to visually indicate depths of objects in the surgical area in any suitable way, such as by using different greyscale values to represent different depth values.

Images captured by an endoscope (e.g., by endoscope 200) and/or derived from images captured by endoscope 200 (e.g., visible light images and depth images) may be referred to as "endoscopic imagery." Exemplary anatomical visualization systems and methods described herein may be configured to utilize endoscopic imagery to provide visualizations of anatomical structures, such as described herein.

Endoscope 200 shown in FIG. 2 is illustrative of one imaging device that may be used to obtain endoscopic imagery. Any other suitable imaging device or combination of devices from which visible light data and depth data of a surgical area may be obtained or derived during a surgical procedure may be used in other examples.

Figure 3:
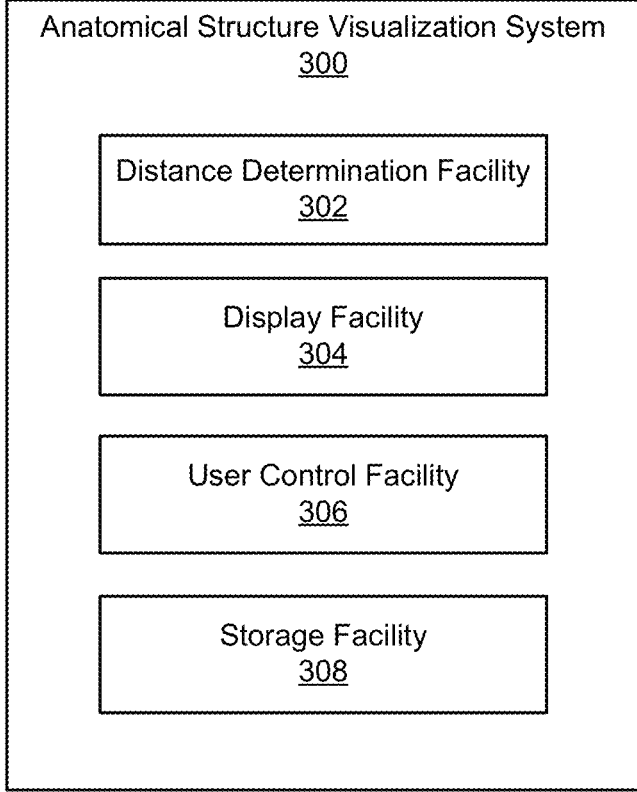
FIG. 3 illustrates an exemplary anatomical structure visualization system according to principles described herein.

FIG. 3 shows an exemplary anatomical structure visualization system 300 ("visualization system 300" or "system 300") configured to provide a visualization of an anatomical structure at a surgical area for use by one or more surgical team members during a surgical procedure. As shown, system 300 may include, without limitation, a distance determination facility 302, a display facility 304, a user control facility 306, and a storage facility 308 selectively and communicatively coupled to one another. It will be recognized that although facilities 302 through 308 are shown to be separate facilities in FIG. 3, facilities 302 through 308 may be combined into fewer facilities, such as into a single facility, or divided into more facilities as may serve a particular implementation. Each of facilities 302 through 308 may be implemented by any suitable combination of computing hardware and/or software. In alternative embodiments, one or more of facilities 302 through 308 may be omitted from system 300 and/or one or more additional facilities may be included in system 300.

System 300 may be associated with a computer-assisted surgical system such as surgical system 100 in any suitable manner. For example, system 300 may be implemented by or included within a computer-assisted surgical system. To illustrate, system 300 may be implemented by one or more computing devices included within manipulating system 102, user control system 104, and/or auxiliary system 106 of surgical system 100. In some examples, system 300 may be at least partially implemented by one or more computing devices communicatively coupled to, but not included in, a computer-assisted surgical system (e.g., one or more servers communicatively coupled to surgical system 100 by way of a network).

Distance determination facility 302 may be configured to perform one or more operations to determine distances between surface anatomy that is visible to an endoscope and embedded anatomy that may be hidden from the view of the endoscope by the surface anatomy. As described herein, such a distance may be a linear distance, within a 3D space, between a point on the surface anatomy and a point on the embedded anatomy. As will also be described herein, the point on the surface anatomy and the point on the embedded anatomy may be associated with a pixel of an image, and system 100 may utilize the determined distance between the points to determine a display parameter for the pixel of the image.

In certain examples, to facilitate determining distances between surface anatomy and embedded anatomy, distance determination facility 302 may access endoscopic imagery of a surgical area of a patient, which imagery may include visible light images, depth images, and metadata for the images. The metadata may include any information associated with the images, such as a position of an endoscope from which endoscopic images are captured, camera parameters (e.g., intrinsic and/or extrinsic camera parameters), a reference frame of the endoscope, etc. Distance determination facility 302 may access the endoscopic imagery in any suitable way from any suitable source, such as directly or indirectly from an endoscope that captures images of a surgical area in real time during a surgical procedure.

Distance determination facility 302 may also access model data representative of modeled anatomy of the patient. The model data may represent a model of anatomy associated with the surgical area of the patient, such as a model of embedded anatomy that may be hidden from the view of the endoscope by surface anatomy. The model of the anatomy may be generated at any suitable time, including in advance of or as part of a surgical procedure and/or in advance of or concurrently with the capture of endoscopic imagery. The model of the anatomy may include any suitable three-dimensional model of the anatomy represented in any suitable data format (e.g., using a Digital Imaging and Communications in Medicine (DICOM) standard specifying a file format definition and/or network communication protocol for medical imaging data). The model may include a model, or a set of segmented models, generated from any suitable 3D imaging procedure, such as a computed tomography (CT) scan, a segmented DICOM scan, a magnetic resonance imaging (MRI) scan, fluorescence imaging, infrared or near-infrared imaging, imaging showing dye or other markers, or the like.

Distance determination facility 302 may register the endoscopic imagery and the model of anatomy to a common 3D space and/or reference frame in any suitable way, such as by aligning anatomical anchor points in the endoscopic imagery and/or modeled anatomy. In certain examples, distance determination facility 302 may perform one or more operations to register the model of the anatomy with a reference frame of the endoscope that captured the endoscopic imagery.

By registering the endoscopic imagery and the model of anatomy to a common 3D space and/or reference frame, distance determination facility 302 may generate a converged model in which both the endoscopic imagery and the model of anatomy are represented in a common 3D space. In other examples, registration of the endoscopic imagery and the model of anatomy to a common 3D space and/or reference frame may be performed outside of system 300. In such examples, distance determination facility 302 may simply access data representative of the converged model from a suitable source.

Distance determination facility 302 may use the converged model to determine distances between surface anatomy visible to the endoscope and modeled anatomy, such as embedded anatomy that is occluded from the view of the endoscope by the surface anatomy. Distance determination facility 302 may determine such distances in any suitable way. An exemplary way of determining such distances will now be described with reference to FIG. 4.

Figure 4:
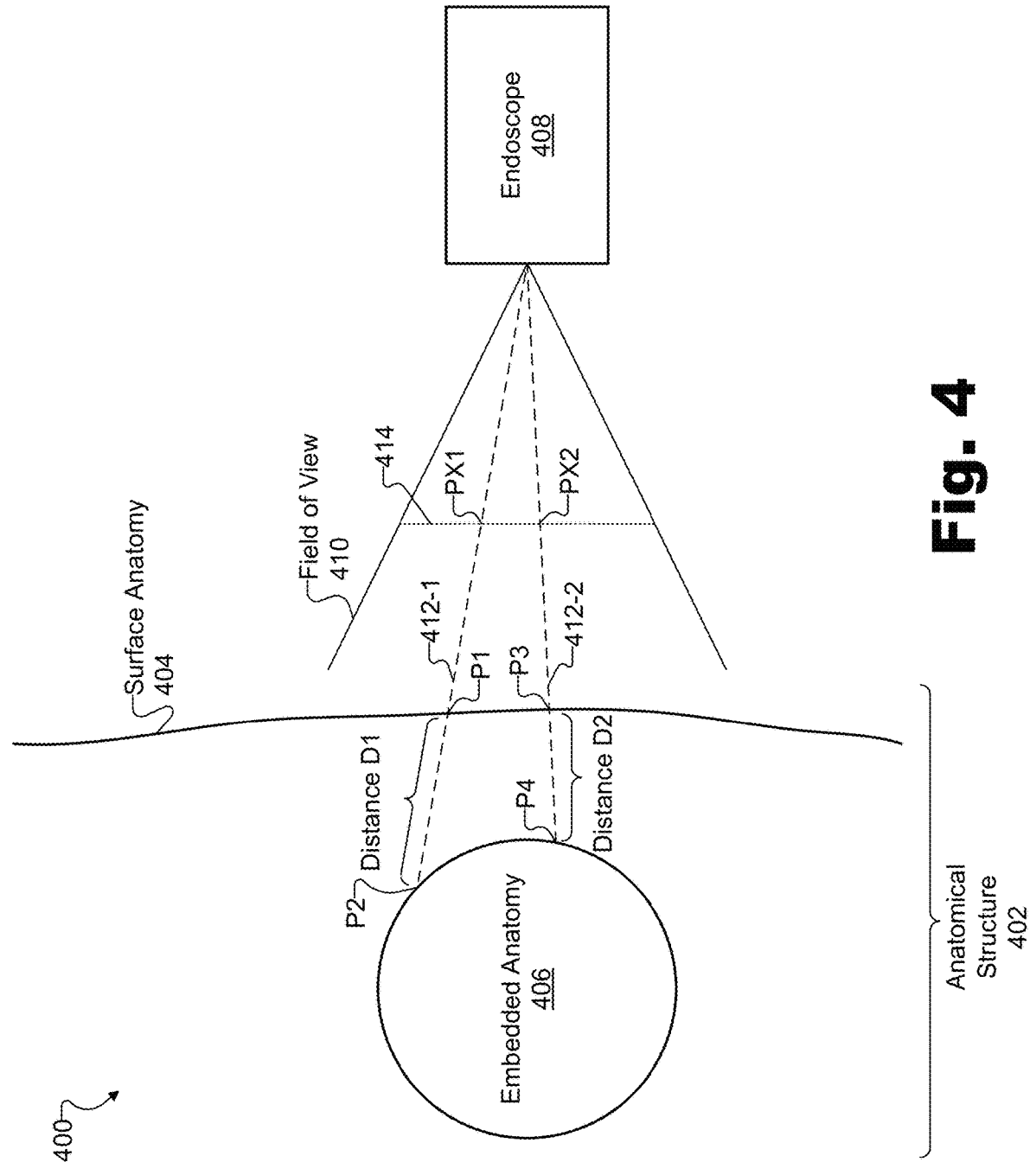
FIG. 4 illustrates an exemplary configuration that includes an anatomical structure of which the anatomical structure visualization system of FIG. 1 may provide a visualization according to principles described herein.

FIG. 4 illustrates an exemplary configuration 400 that includes an anatomical structure 402 of which system 100 may provide a visualization. As shown, anatomical structure 402 includes surface anatomy 404 and embedded anatomy 406. Surface anatomy 404 includes an anatomical surface that may be visible to an endoscope 408 positioned as shown in FIG. 4 (e.g., positioned at a surgical area during a surgical procedure). The anatomical surface may include at least a portion of surface anatomy 404 that is within a field of view 410 of endoscope 408. Embedded anatomy 406 may include an anatomical object that is embedded within surface anatomy 404 or otherwise occluded from the view of endoscope 408 by surface anatomy 404.

Anatomical structure 402 may be represented by a converged model as described above. For example, endoscope 408 may capture endoscopic imagery of the anatomical surface that is visible to endoscope. Using depth data included in or otherwise associated with the endoscopic imagery, a 3D model of the anatomical surface may be generated, such as a depth map of the anatomical surface. Distance determination facility 302 may register the 3D model of the anatomical surface and a 3D model of the embedded anatomical object to a common 3D space or reference frame to form a converged model that represents the anatomical structure 402 in the common 3D space or reference frame.

Distance determination facility 302 may use the converged model representing anatomical structure 402 to determine distances between surface anatomy 404 visible to endoscope 408 and embedded anatomy 406. In certain examples, Distance determination facility 302 may determine such a distance along a line extending from a viewpoint of endoscope 408 in the common 3D space. For example, dashed line 412-1 represents a line extending from the viewpoint of endoscope 408 and intersecting a point P1 on surface anatomy 404 and a point P2 on embedded anatomy 406. Distance determination facility 302 may determine a distance D1 between point P1 on surface anatomy 404 and point P2 on embedded anatomy 406. Distance determination facility 302 may similarly determine distances along other lines extending from the viewpoint of endoscope 408 in the common 3D space. For example, dashed line 412-2 represents a line extending from the viewpoint of endoscope 408 and intersecting a point P3 on surface anatomy 404 and a point P4 on embedded anatomy 406. Distance determination facility 302 may determine a distance D2 between point P3 on surface anatomy 404 and point P4 on embedded anatomy 406.

In certain examples, lines 412-1 and 412-2 may represent image projection rays, such as perspective image projection rays projected from a viewpoint of endoscope 408 and through points (e.g., pixels) on an image plane 414. In such examples, distances D1 and D2 may represent depths, along perspective image projection rays, from surface anatomy 404 to embedded anatomy 406.

FIG. 4 illustrates one exemplary way that distance determination facility 302 may determine distances between surface anatomy 404 visible to an endoscope and embedded anatomy 406 occluded from the view of the endoscope by surface anatomy 404. In other examples, distance determination facility 302 may be configured to determine distances between surface anatomy 404 visible to an endoscope and embedded anatomy 406 occluded from the view of the endoscope by surface anatomy 404 in any other suitable way, such as by using orthographic projection rays as lines along which to identify corresponding points on surface anatomy 404 and embedded anatomy 406 and to determine distances between the corresponding points.

Returning to FIG. 3, display facility 304 may be configured to provide a visualization of an anatomical structure based on distances, determined by distance determination facility 302, between surface anatomy visible to an endoscope and embedded anatomy occluded from the view of the endoscope by the surface anatomy. To this end, for example, display facility 304 may be configured to determine, based on determined distances between surface anatomy and embedded anatomy included in an anatomical structure, display parameters for pixels of an image representative of a view of the anatomical structure, such as an image representative of a view of the surface anatomy from the viewpoint of an endoscope.

FIG. 4 shows pixels PX1 and PX2 included in image plane 414. Pixel PX1, point P1, and point P2 are intersected by line 412-1, and pixel PX2, point P3, and point P4 are intersected by line 412-2. Based on these linear relationships, pixel PX1 may be said to correspond to point P1 on surface anatomy 404 and point P2 on embedded anatomy 406, and pixel PX2 may be said to correspond to point P3 on surface anatomy 404 and point P4 on embedded anatomy 406. Display facility 304 may determine a display parameter for pixel PX1 based on distance D1 between points P1 and P2 and on display parameters associated with points P1 and/or P2. Display facility 304 may similarly determine a display parameter for pixel PX2 based on distance D2 between points P3 and P4 and on display parameters associated with points P3 and/or P4.

For a pixel on image plane 414 that corresponds to a point on surface anatomy 404 and a point on embedded anatomy 406, display facility 304 may determine a display parameter for the pixel in a manner configured to selectively visualize the point on embedded anatomy 406 as being embedded within surface anatomy 404. The display parameter may include any parameter configured to differentiate the visual appearance of the pixel from one or more other pixels of an image so as to visually indicate an existence and/or one or more properties of the point on embedded anatomy 406. The display parameter may include a color, an opacity, a transparency, a saturation, a brightness, and/or any other display parameter for the pixel. The display parameter may also include any combination or sub-combination of such parameters.

In certain examples, display facility 304 may be configured to determine a display parameter for a pixel of the image based on a determined distance and using a defined function that specifies how the display parameter changes for different values of the determined distance. The defined function may be any suitable linear or non-linear function and may be defined as may suit particular implementation.

Figure 5:
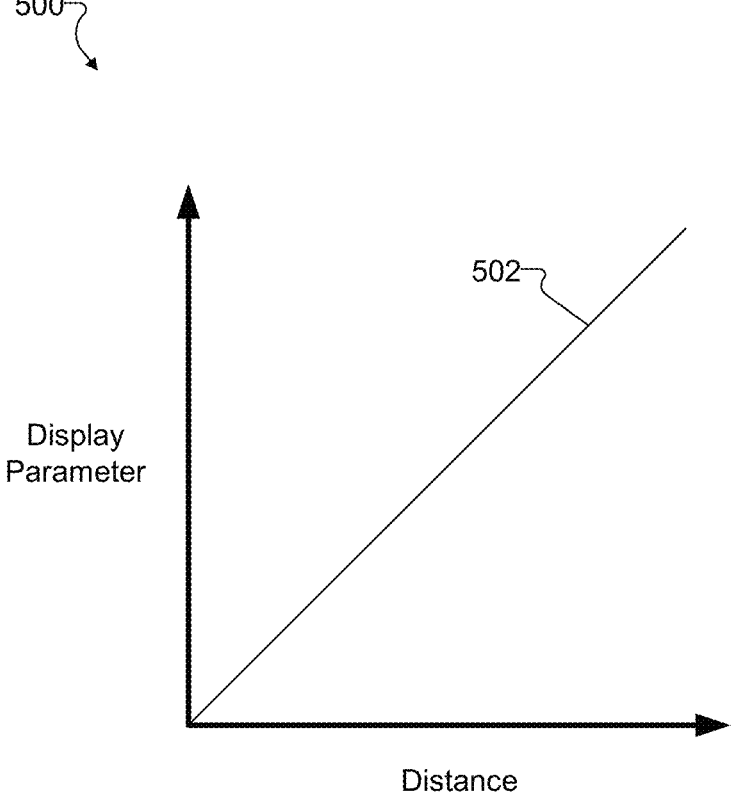
FIGS. 5-6 illustrate exemplary functions specifying how a display parameter changes for various distances between surface anatomy and embedded anatomy according to principles described herein.
Figure 6:
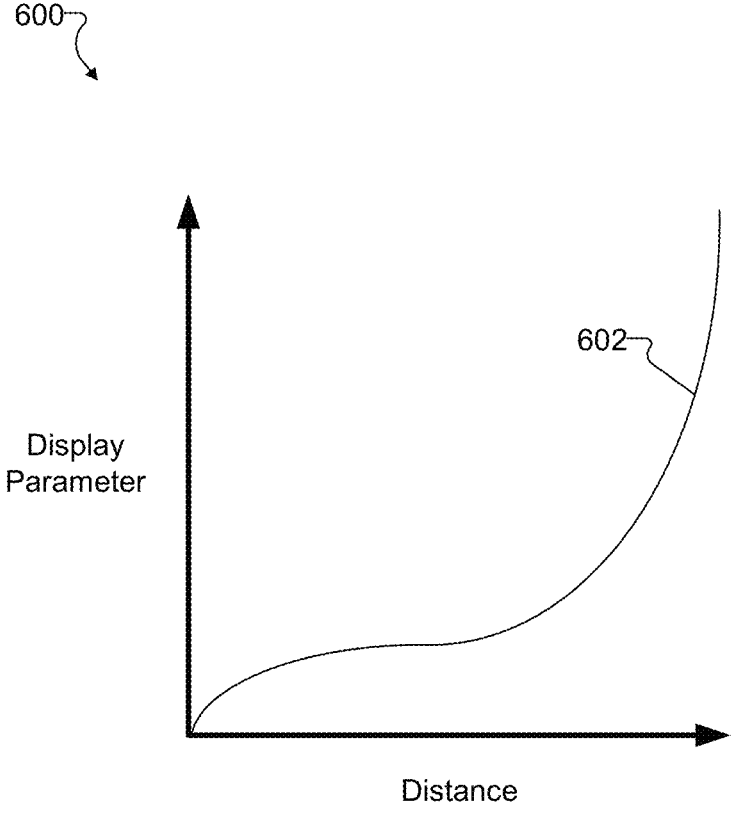

FIG. 5 illustrates a graph 500 of a linear function 502 that specifies values of a display parameter to be determined for different distances. FIG. 6 illustrates a graph 600 of a non-linear function 602 that specifies values of a display parameter to be determined for different distances. Functions 502 and 602 are illustrative of certain examples. Any other suitable function that specifies how a display parameter changes for various determined distances may be used in other examples. For example, any suitable falloff function may be used that defines relationships between a display parameter and distances between anatomical 3D models.

In certain examples, display facility 304 may be configured to determine a display parameter such as a color for a pixel of an image based on a defined color blending function. For example, using the color blending function and based on a determined distance between a point on surface anatomy 404 and a point on embedded anatomy 406, display facility 304 may blend a color associated with the point on embedded anatomy 406 with a color associated with the point on surface anatomy 404 to determine the color for the pixel of the image. The color blending function may be defined to give the color associated with the point on embedded anatomy 406 more weight when the determined distance is relatively shorter and less weight when the determined distance is relatively longer. Thus, for a relatively shorter distance, the color associated with the point on embedded anatomy 406 may be emphasized more in the determined color for the pixel of the image than for a relatively longer distance. To this end, the color blending function may specify how the weight given to the color associated with the point on embedded anatomy 406 changes for different values of the determined distance.

In certain examples, display facility 304 may be configured to determine a display parameter for a pixel of an image based on a parameter of a corresponding point on embedded anatomy 406. To this end, for example, display facility 304 may be configured to determine a blend parameter for the point on embedded anatomy 406 based on the determined distance between the point on embedded anatomy 406 and a corresponding point on surface anatomy 404. For example, using a defined blend function and based on the determined distance, display facility 304 may determine a blend parameter for the point on embedded anatomy 406. The blend function may specify how the blend parameter changes for different values of the determined distance.

Once the blend parameter for the point on embedded anatomy 406 is determined, display facility 304 may determine the display parameter for the pixel of the image based on the blend parameter. In certain examples, display facility 304 may be configured to give more weight to one or more display parameters associated with the point on embedded anatomy 406 when the determined blend parameter for the point is relatively higher (e.g., based on a relatively shorter determined distance) and less weight to the one or more display parameters associated with the point when the determined blend parameter for the point if relatively lower (e.g., based on a relatively larger determined distance). Thus, for a relatively higher blend parameter, a display parameter associated with the point on embedded anatomy 406 may be emphasized more in the determined display parameter for the pixel of the image than for a relatively lower blend paramter.

In certain examples, display facility 304 may be configured to determine a display parameter for a pixel of an image based on a defined maximum distance. For example, for a point on embedded anatomy 406, display facility 304 may be configured to determine the display parameter for the corresponding pixel of the image based on a maximum distance beyond which the point on embedded anatomy 406 is not visually represented by the pixel of the image and within which the point on embedded anatomy 406 is visually represented by the pixel of the image. To this end, in certain examples, display facility 304 may be configured not to blend a display parameter of the point on embedded anatomy 406 with a display parameter of a corresponding point on surface anatomy 404 when the determined distance between the points is greater than the defined maximum distance, such that the point on embedded anatomy 406 will not be represented in the pixel of the image when the point on embedded anatomy 406 is too deep, i.e., beyond the maximum distance, from the corresponding point on surface anatomy 404. Thus, the maximum distance may provide a limited depth range within which embedded anatomy 406 will be visually represented in an image and beyond which embedded anatomy 406 will not be visually represented in the image.

In certain examples, display facility 304 may be configured to determine a display parameter for a pixel of an image based on a defined minimum visualization threshold for embedded anatomy. For example, for a point on embedded anatomy 406, display facility 304 may be configured to determine the display parameter for the corresponding pixel of the image based on a minimum visualization threshold at which the point on embedded anatomy 406 may be visually represented by the pixel of the image. To this end, in certain examples, display facility 304 may be configured to determine the display parameter to provide a visual emphasis that provides at least the minimum visualization threshold. In certain examples, display facility 304 may be configured to satisfy the minimum visualization threshold using a minimum visibility parameter such as a minimum opacity parameter allowed for the point on embedded anatomy 406. In such examples, display facility 304 may set the opacity parameter for the point on embedded anatomy 406 to at least satisfy the minimum allowed opacity parameter.

In certain examples, any combination or sub-combination of color blending functions, color parameters, blend coefficient functions (e.g., opacity functions), blend parameters (e.g., opacity parameters), maximum distance thresholds, minimum visualization thresholds, and/or other display parameters, display parameter functions, etc. may be used by display facility 304 to determine a display parameter for a pixel of an image in a manner that selectively and visually represents embedded anatomy together with surface anatomy.

In certain examples, for instance, display facility 304 may be configured to determine a color for a pixel of an image based on the following algorithm:

$$\text{PixelColor} = \text{PixelAColor.Blend}(\text{AColor}, \text{EColor}, \text{BlendCoeff})$$

In the algorithm, "PixelColor" is the determined color for the pixel, "PixelAColor.Blend" is a color blending function, "AColor" is a color of a pixel point on surface anatomy captured by an endoscope, "EColor" is a color of a corresponding pixel point on a model of embedded anatomy, and "BlendCoeff" is a color blending coefficient that may be determined by display facility 304. Based on the algorithm, display facility 304 may blend colors (e.g., RGB values) of the color of the pixel point on the surface anatomy with the color of the pixel point on the embedded anatomy based on blend coefficient "BlendCoeff."

In certain examples, display facility 304 may determine "BlendCoeff" based on the following algorithm:

$$BlendCoeff=Max(MinCE,FalloffFunction(D,MaxD)).$$

In this blend coefficient algorithm, "BlendCoeff" is the determined blend coefficient, "MinCE" is a minimal level of visibility for the embedded anatomy, "D" is a determined distance between the point on the surface anatomy and the corresponding point on the embedded anatomy, "MaxD" is a maximum depth to normalize distance to (e.g., representing how deep into tissue will be visualized), "FalloffFunction" is a function the defines how the color of embedded anatomy decreases as the determined distance "D" gets closer to the maximum depth "MaxD" (e.g., how the determined distance "D" is translated to a value between 0-1), and "Max" will not allow BlendCoeff to become smaller than MinCE.

The above-described algorithms illustrate one example of how display facility 304 may determine a color for a pixel of an image in a manner that visualizes depth of embedded anatomy together with surface anatomy. Other suitable algorithms for determining a display parameter for a pixel of an image to visualize depth of embedded anatomy may be used in other examples. Such algorithms may blend display parameter values from two or more anatomical 3D model layers to determine a blended display parameter (e.g. a blended color), the blended display parameter determined based on a depth or depths between the 3D model layers.

Once display facility 304 determines a display parameter (e.g., a blended color) for a pixel of an image, display facility 304 may assign the display parameter to the pixel of the image. The assignment may be made in any way suitable for rendering and/or display of the pixel of the image to be based on the assigned display parameter.

Display facility 304 may determine and assign display parameters for all pixels of an image. Display facility 304 may provide the image for rendering and/or display by a display device. When displayed, the image may provide a visualization of depths of embedded anatomy from surface anatomy, including a visualization of differences in depths between different points on embedded anatomy.

Returning to FIG. 4, distance D2 is shorter than distance D1. Accordingly, display facility 304 may determine and assign display parameters to pixels PX2 and PX1 in a way that will visually emphasize, within an image, point P4 more than point P2 based on point P4 being closer than point P2 to surface anatomy 404 from the perspective that the image is rendered (e.g., from the perspective of endoscope 408). For example, a color of point P4 may be blended into the color of pixel PX2 more than a color of point P2 is blended into the color of pixel PX1, which may visually emphasis point P4 more than point P2 in the image.

By basing the visual emphasis of embedded anatomy 406 on point-by-point distances, such as distances D1 and D2, between embedded anatomy 406 and surface anatomy 404, display facility 304 may determine display parameters for pixels of an image in a manner that may visualize the point-by-point depths of embedded anatomy 406 in the image. In certain examples, such an image may provide a visualization of a pixel-by-pixel topographic representation of embedded anatomy 406 in the image, together with a visualization of surface tissue captured by an endoscope. In this or another manner, the image may provide a visualization of an anatomical structure having anatomical components that are visible to and other anatomical components that are hidden from the viewpoint of an endoscope located at a surgical site during a surgical procedure.

In certain implementations, display facility 304 may provide an image for display as part of a sequence of images such as video images of a surgical area. Display facility 304 may be configured to generate video images in real time such that the video images visually represent real-time depths of embedded anatomy 406 relative to surface anatomy 404 visible to endoscope 408. Accordingly, as a surgical team member controls and moves endoscope 408 (e.g., a position and/or orientation of endoscope 408) relative to a surgical area, system 100 may continually determine distances between embedded anatomy 406 and surface anatomy 404 and determine, based on the distances, display parameters for pixels of video images such that each frame of the video provides a real-time visualization of depths of embedded anatomy 406 relative to surface anatomy 404.

Returning to FIG. 3, user control facility 306 may be configured to provide one or more controls for use by a user of system 300 to adjust one or more settings used by display facility 304 to determine a display parameter based on a determined distance between embedded anatomy and surface anatomy. The user controls may be provided in any way suitable for use by a user of system 300, such as for use by a surgical team member who uses computer-assisted surgical system 100, to provide user input to adjust one or more settings used by display facility 304 to determine a display parameter. In certain examples, the user controls may be configured to facilitate user input to adjust the display parameter in real time during a surgical procedure in order to modify how depth of embedded anatomy is visually indicated in an image. In some implementations, the user controls may be provided as controls (e.g., as master controls) of user control system 104 of computer-assisted surgical system 100. For example, such user controls may be provided, on user control system 104, as a slider user input mechanism that facilitates user input to adjust a display parameter setting to a value within a range of available values for the display parameter. Such a slider input mechanism may facilitate a user-controlled gradual transition (e.g. a fade-in/fade out of embedded anatomy) or crossfade between visualization of surface anatomy and embedded anatomy.

As an example, a user control may allow a surgical team member to adjust a maximum depth (e.g., MaxD in an algorithm described above) within which embedded anatomy is visually represented in an image and beyond which an embedded anatomy is not visually represented in an image. This may allow a surgical team member to control how deep beyond visible surface tissue that embedded anatomy will be visualized. As another example, a user control may allow a surgical team member to adjust a minimum visualization threshold (e.g., MinCE in an algorithm described above) for embedded anatomy. This may allow the surgical team member to control a minimum allowable visual emphasis (e.g., a minimum opacity) that is to be displayed for embedded anatomy. As another example, a user control may allow a surgical team member to adjust a prominence multiplier that adjusts a degree of visual emphasis that is used to visually represent embedded anatomy in an image. This may allow the surgical team member to control how prominently embedded anatomy is visually emphasized in an image.

By providing such user controls for use by a surgical team member, the surgical team member may intuitively and conveniently adjust settings for visualization of embedded anatomy to fit a particular situation, configuration, and/or need during a surgical procedure. For example, if a surgeon wants to focus attention on surface anatomy and embedded anatomy immediately beneath surface anatomy, the surgeon may utilize a user control to adjust a maximum distance threshold (e.g., MaxD) to a small value that will result in only embedded anatomy immediately beneath surface anatomy being visualized in an image.

In certain examples, user control facility 306 may be configured to provide one or more controls for use by a user of system 300 to toggle between different display modes provided by system 300 and/or computer-assisted surgical system 100. The user controls may be provided in any way suitable for use by a user of system 300, such as for use by a surgical team member who uses computer-assisted surgical system 100, to provide user input to toggle between display modes. In certain examples, the user controls may be configured to facilitate user input to toggle between display modes in real time during a surgical procedure. In some implementations, a toggle, slide, or other control may be provided as a control of (e.g., a master control of) user control system 104 of computer-assisted surgical system 100.

In certain examples, a user control for toggling between display modes may facilitate user input to toggle between a mode for visualization of only surface anatomy visible to an endoscope, a mode for concurrent visualization of surface anatomy visible to the endoscope and embedded anatomy, and a mode for visualization of only embedded anatomy. In the mode for visualization of only visible surface anatomy, display facility 304 may provide images that display representations of surface anatomy that is visible to an endoscope without incorporating any visual representation of embedded anatomy that is occluded from the view of the endoscope. In the mode for concurrent visualization of surface anatomy visible to the endoscope and embedded anatomy, display facility 304 may provide images that display visual representations of surface anatomy that is visible to an endoscope together with visual representations of anatomy embedded within the surface anatomy or otherwise hidden from the view of the endoscope by the surface anatomy. In the mode for visualization of only embedded anatomy, display facility 304 may provide images that display representations of embedded anatomy without representations of anatomy that is visible to an endoscope. In the mode for visualization of only embedded anatomy, system 300 and/or system 100 may provide one or more user control lockout features that prevent a user from using certain user controls while only embedded anatomy is displayed, so as to help prevent an error from being made while surface anatomy that is visible to an endoscope is not being displayed.

Storage facility 308 may store any data received, generated, managed, maintained, used, and/or transmitted by facilities 302 through 306 in a particular implementation. For example, storage facility 308 may store program instructions (e.g., computer code) for performing operations described herein, model data representing a model of anatomy (e.g., a 3D model of anatomy), endoscopic imagery data representing endoscopic imagery, data representing determined display parameters, image data representing generated images, and/or any other data as may serve a particular implementation.

Figure 7:
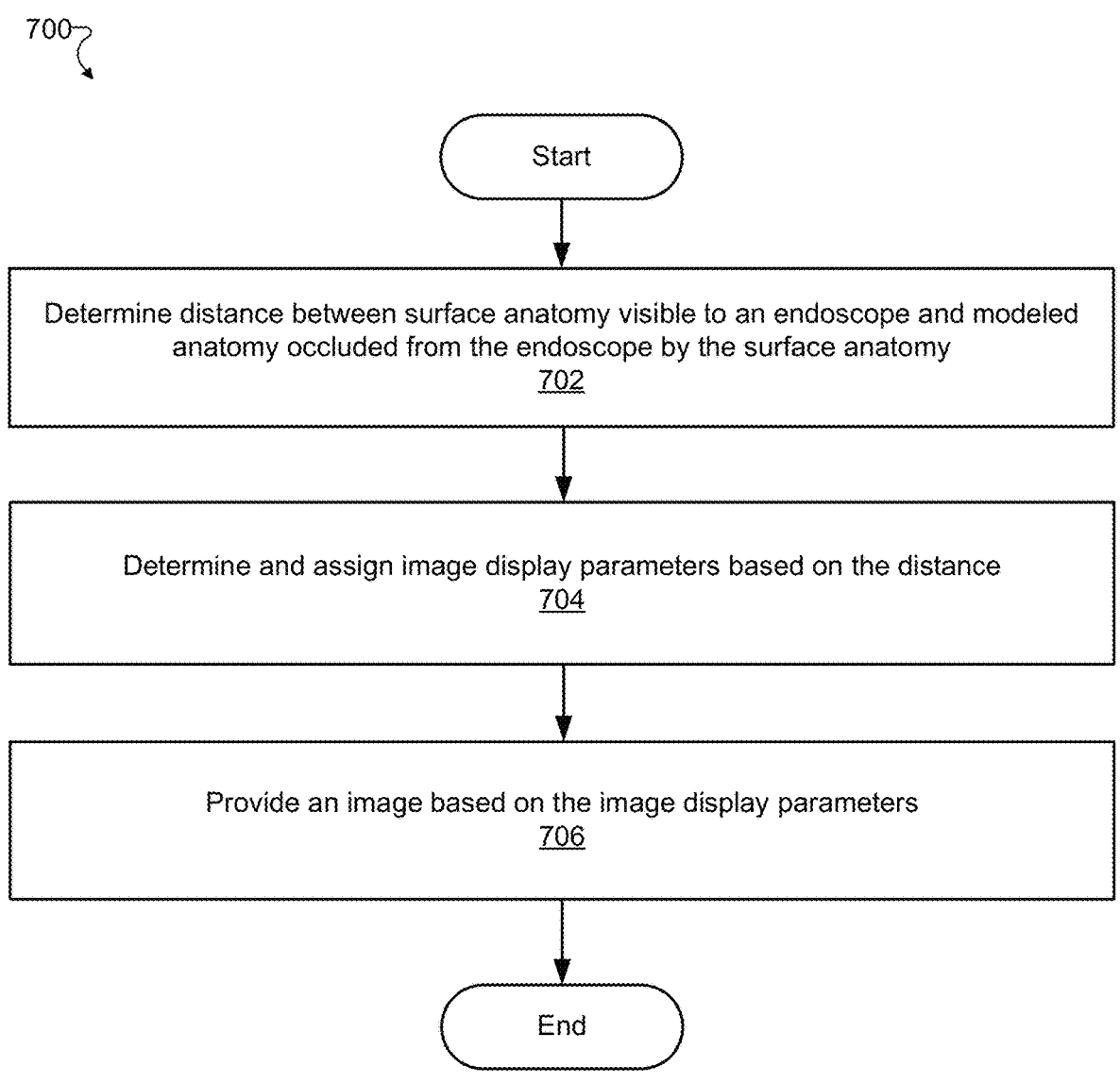
FIG. 7 illustrates an exemplary anatomical structure visualization method according to principles described herein.

FIG. 7 illustrates an exemplary anatomical structure visualization method 700. While FIG. 7 illustrates exemplary operations according to one embodiment, other embodiments may omit, add to, reorder, and/or modify any of the operations shown in FIG. 7. One or more of the operations shown in FIG. 7 may be performed by an anatomical structure visualization system such as system 300, any components included therein, and/or any implementation thereof.

In operation 702, an anatomical structure visualization system may determine distance between surface anatomy visible to an endoscope and embedded anatomy occluded from the endoscope by the surface anatomy. Operation 702 may be performed in any of the ways described herein, including by the anatomical structure visualization system using a converged model that includes endoscopic imagery of a patient and modeled anatomy of the patient registered to a common 3D space or reference frame to determine the distance, which may include a distance, along a line extending from a viewpoint of the endoscope in the 3D space, between a point on the surface anatomy and a point on the modeled anatomy.

In operation 704, the anatomical structure visualization system may determine and assign image display parameters based on the distance determined in operation 702. Operation 704 may be performed in any of the ways described herein, including by the anatomical structure visualization system determining and assigning display parameters for pixels of an image representative of an anatomical structure, such as an image representative of a view of the surface anatomy from the viewpoint of the endoscope.

In operation 706, the anatomical structure visualization system may provide the image, for display, based on the display parameters. Operation 704 may be performed in any of the ways described herein. As described herein, the image may provide a visualization of the embedded anatomy together with the surface anatomy from the viewpoint of the endoscope, where the image visualizes how deep the embedded anatomy is positioned from the surface anatomy.

Method 700 may be continually repeated to generate and provide, in real time during a surgical procedure, images as frames of video of a surgical area during the surgical procedure. Accordingly, the video may assist a surgical team member in performing the surgical procedure, such as by visualizing, to the surgical team member in real time, how deep embedded anatomy not visible to an endoscope is located from surface anatomy visible to the endoscope.

While the video is being generated and presented in real time during the surgical procedure, the surgical team member may utilize a user control to adjust a setting used to determine how to represent the embedded anatomy. In response to the adjusted setting, the anatomical structure visualization system may modify, in real time how embedded anatomy is represented in the video, such as by changing how one or more display parameters are determined for the video.

Certain operations are described herein as being able to be performed in real time in some examples. Operations may be performed in real time or near real time when they are performed immediately and without undue delay such that, for example, data processing operations associated with an ongoing event or procedure (e.g., a surgical procedure) are performed without undue delay even if there is some amount of processing delay.

While certain examples described herein are directed to determining a display parameter for a pixel of an image based on a point on surface anatomy and a point on a modeled, embedded anatomical object, in certain examples, system and methods described herein may determine a display parameter for a pixel of an image, in any of the ways described herein, based on a point on surface anatomy and multiple points on one or more modeled, embedded anatomical objects, depending on a number, shape, and/or configuration of modeled, embedded anatomical objects relative to the surface anatomy and viewpoint of an endoscope.

In certain examples, the visualization of embedded anatomy, as described herein, may assist a surgical team member in performing a surgical procedure in one or more ways. For example, a surgeon may intuitively, conveniently, and/or accurately navigate surgical tools at a surgical area and/or manipulate tissue at a surgical area. Visualizations described herein may present helpful information, such as locations of embedded anatomical landmarks, in intuitive and natural ways that assist the surgeon and without overloading the surgeon with too much information.

Visualizations such as the exemplary visualizations described herein may provide one or more advantages and/or benefits compared to conventional technologies for displaying multiple layers of anatomy, including any of the advantages and/or benefits described or made apparent herein. Certain conventional technologies that overlay modeled anatomy are not aware of and do not visualize depth of the modeled anatomy from surface anatomy. For example, using conventional technologies, a model of a blood vessel may be simply overlaid on imagery of surface tissue that is visible to an endoscope without providing any information about how deep the blood vessel is embedded behind the surface tissue.

In certain embodiments, one or more of the systems, components, and/or processes described herein may be implemented and/or performed by one or more appropriately configured computing devices. To this end, one or more of the systems and/or components described above may include or be implemented by any computer hardware and/or computer-implemented instructions (e.g., software) embodied on at least one non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), electrically erasable programmable read-only memory ("EPROM"), FLASH-EEPROM, any other memory chip or cartridge, or any other tangible medium from which a computer can read.

Figure 8:
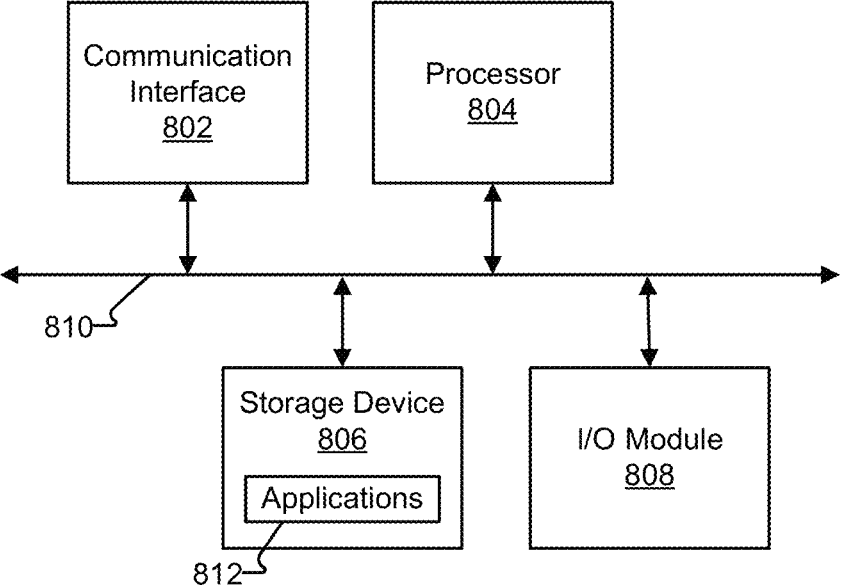
FIG. 8 illustrates an exemplary computing device according to principles described herein.

FIG. 8 illustrates an exemplary computing device 800 that may be specifically configured to perform one or more of the processes described herein. As shown in FIG. 8, computing device 800 may include a communication interface 802, a processor 804, a storage device 806, and an input/output ("I/O") module 808 communicatively connected via a communication infrastructure 810. While an exemplary computing device 800 is shown in FIG. 8, the components illustrated in FIG. 8 are not intended to be limiting. Additional or alternative components may be used in other embodiments. Components of computing device 800 shown in FIG. 8 will now be described in additional detail.

Communication interface 802 may be configured to communicate with one or more computing devices. Examples of communication interface 802 include, without limitation, a wired network interface (such as a network interface card), a wireless network interface (such as a wireless network interface card), a modem, an audio/video connection, and any other suitable interface.

Processor 804 generally represents any type or form of processing unit capable of processing data or interpreting, executing, and/or directing execution of one or more of the instructions, processes, and/or operations described herein. Processor 804 may direct execution of operations in accordance with one or more applications 812 or other computer-executable instructions such as may be stored in storage device 806 or another computer-readable medium.

Storage device 806 may include one or more data storage media, devices, or configurations and may employ any type, form, and combination of data storage media and/or device. For example, storage device 806 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 806. For example, data representative of one or more executable applications 812 configured to direct processor 804 to perform any of the operations described herein may be stored within storage device 806. In some examples, data may be arranged in one or more databases residing within storage device 806.

I/O module 808 may include one or more I/O modules configured to receive user input and provide user output. One or more I/O modules may be used to receive input for a single virtual reality experience. I/O module 808 may include any hardware, firmware, software, or combination thereof supportive of input and output capabilities. For example, I/O module 808 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 808 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 808 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 800. For example, one or more applications 812 residing within storage device 806 may be configured to direct processor 804 to perform one or more processes or functions associated facilities 302 through 306 of system 300. Likewise, storage facility 308 of system 300 may be implemented by storage device 806 or a component thereof.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A computer-assisted surgical system comprising:
at least one physical computing device communicatively coupled to an endoscope and a display device, the at least one physical computing device configured to:
determine, based on a distance between a point on an anatomical surface visible to the endoscope and a point on an embedded anatomical object visually occluded from a viewpoint of the endoscope by the anatomical surface, a blend parameter;
determine, based on the blend parameter, the point on the anatomical surface, and the point on the embedded anatomical object, a display parameter for a pixel of an image, the pixel corresponding to the point on the anatomical surface; and
provide the image for display by the display device, the image including the pixel displayed in accordance with the display parameter, the image comprising a view of the anatomical surface from the viewpoint of the endoscope and a visualization of the embedded anatomical object.

2. The computer-assisted surgical system of claim 1, wherein the at least one physical computing device is configured to determine the blend parameter further based on data that maps different blend parameter values to different distances between the point on the anatomical surface and the point on the embedded anatomical object.

3. The computer-assisted surgical system of claim 1, wherein the at least one physical computing device is configured to determine the blend parameter using a function that specifies how the blend parameter changes as the distance between the point on the anatomical surface and the point on the embedded anatomical object changes.

4. The computer-assisted surgical system of claim 1, wherein the at least one physical computing device is configured to determine the display parameter further based on a maximum distance beyond which the point on the embedded anatomical object is not visually represented by the pixel of the image and within which the point on the embedded anatomical object is visually represented by the pixel of the image.

5. The computer-assisted surgical system of claim 1, wherein the at least one physical computing device is configured to determine the display parameter further based on a minimum visibility parameter allowed for the point on the embedded anatomical object.

6. The computer-assisted surgical system of claim 1, wherein the at least one physical computing device is configured to determine the display parameter further based on data that maps different weights to be given to a color associated with the embedded anatomical object to different distances between the point on the anatomical surface and the point on the embedded anatomical object.

7. The computer-assisted surgical system of claim 1, wherein the at least one physical computing device is configured to determine the display parameter further based on a color blending function that specifies how a weight given to a color associated with the embedded anatomical object changes for different values of the distance between the point on the anatomical surface and the point on the embedded anatomical object.

8. The computer-assisted surgical system of claim 1, wherein the display parameter for the pixel of the image comprises a color for the pixel that is a result of blending, based on the blend parameter, a color associated with the point on the embedded anatomical object and a color associated with the point on the anatomical surface.

9. The computer-assisted surgical system of claim 1, wherein, to determine the display parameter for the pixel of the image, a color associated with the embedded anatomical object is given more weight when the blend parameter is relatively higher and less weight when the blend parameter is relatively lower.

10. A method comprising:
determining, by an anatomical structure visualization system and based on a distance between a point on an anatomical surface visible to an endoscope and a point on an embedded anatomical object visually occluded from a viewpoint of the endoscope by the anatomical surface, a blend parameter;
determining, by the anatomical structure visualization system and based on the blend parameter, the point on the anatomical surface, and the point on the embedded anatomical object, a display parameter for a pixel of an image, the pixel corresponding to the point on the anatomical surface; and
providing, by the anatomical structure visualization system, the image for display by a display device, the image including the pixel displayed in accordance with the display parameter, the image comprising a view of the anatomical surface from the viewpoint of the endoscope and a visualization of the embedded anatomical object.

11. The method of claim 10, wherein the determining of the blend parameter is further based on data that maps different blend parameter values to different distances between the point on the anatomical surface and the point on the embedded anatomical object.

12. The method of claim 10, wherein the determining of the blend parameter uses a function that specifies how the blend parameter changes as the distance between the point on the anatomical surface and the point on the embedded anatomical object changes.

13. The method of claim 10, wherein the determining of the display parameter is further based on a maximum distance beyond which the point on the embedded anatomical object is not visually represented by the pixel of the image and within which the point on the embedded anatomical object is visually represented by the pixel of the image.

14. The method of claim 10, wherein the determining of the display parameter is further based on a minimum visibility parameter allowed for the point on the embedded anatomical object.

15. The method of claim 10, wherein the determining of the display parameter is further based on data that maps different weights to be given to a color associated with the embedded anatomical object to different distances between the point on the anatomical surface and the point on the embedded anatomical object.

16. The method of claim 10, wherein the determining of the display parameter is further based on a color blending function that specifies how a weight given to a color associated with the embedded anatomical object changes for different values of the determined distance.

17. The method of claim 10, wherein the display parameter for the pixel of the image comprises a color for the pixel that is a result of blending, based on the blend parameter, a color associated with the point on the embedded anatomical object and a color associated with the point on the anatomical surface.

18. The method of claim 10, wherein the determining of the display parameter for the pixel of the image comprising giving a color associated with the embedded anatomical object more weight when the blend parameter is relatively higher and less weight when the blend parameter is relatively lower.

19. A non-transitory computer-readable medium storing instructions executable by a processor to:

determine, based on a distance between a point on an anatomical surface visible to an endoscope and a point on an embedded anatomical object visually occluded from a viewpoint of the endoscope by the anatomical surface, a blend parameter;

determine, based on the blend parameter, the point on the anatomical surface, and the point on the embedded anatomical object, a display parameter for a pixel of an image, the pixel corresponding to the point on the anatomical surface; and provide the image for display by a display device, the image including the pixel displayed in accordance with the display parameter, the image comprising a view of the anatomical surface from the viewpoint of the endoscope and a visualization of the embedded anatomical object.

20. The non-transitory computer-readable medium of claim 19, wherein, to determine the display parameter for the pixel of the image, a color associated with the embedded anatomical object is given more weight when the blend parameter is relatively higher and less weight when the blend parameter is relatively lower.

* * * * *